United States Patent
Luschtinetz et al.

(10) Patent No.: US 11,262,304 B2
(45) Date of Patent: Mar. 1, 2022

(54) METHOD FOR DETERMINING THE MIGRATION POTENTIAL OF AN AT LEAST PARTIALLY CURED ENERGY CURING INK AND/OR VARNISH PRINTED ON A SUBSTRATE, AND ESPECIALLY OF A PRINTED FOOD PACKING

(71) Applicant: HUBERGROUP DEUTSCHLAND GmbH, Kirchheim-Heimstetten (DE)

(72) Inventors: Franziska Luschtinetz, Kirchheim-Heimstetten (DE); Carsten Zoelzer, Kirchheim-Heimstetten (DE); Taner Bicer, Kirchheim-Heimstetten (DE)

(73) Assignee: HUBERGROUP DEUTSCHLAND GmbH, Kirchheim-Heimstetten (DE)

( * ) Notice: Subject to any disclaimer, the term of this patent is extended or adjusted under 35 U.S.C. 154(b) by 108 days.

(21) Appl. No.: 16/604,965

(22) PCT Filed: Apr. 11, 2018

(86) PCT No.: PCT/EP2018/059303
§ 371 (c)(1),
(2) Date: Oct. 11, 2019

(87) PCT Pub. No.: WO2018/189248
PCT Pub. Date: Oct. 18, 2018

(65) Prior Publication Data
US 2021/0131965 A1    May 6, 2021

(30) Foreign Application Priority Data
Apr. 11, 2017 (EP) ................................. 17166008

(51) Int. Cl.
*G01N 21/64* (2006.01)
*G01N 1/40* (2006.01)
(Continued)

(52) U.S. Cl.
CPC ....... *G01N 21/6428* (2013.01); *G01N 1/4055* (2013.01); *G01N 21/31* (2013.01);
(Continued)

(58) Field of Classification Search
CPC .. G01N 21/6428; G01N 1/4055; G01N 21/31; G01N 21/8422; G01N 33/32;
(Continued)

(56) References Cited

U.S. PATENT DOCUMENTS

| 5,142,151 A | 8/1992 | Doty et al. |
| 7,043,326 B2 | 5/2006 | Neubauer et al. |

(Continued)

FOREIGN PATENT DOCUMENTS

| CN | 102353662 A | 2/2012 |
| EP | 2133210 A2 | 12/2009 |

(Continued)

OTHER PUBLICATIONS

Snyder RCM Breder CV: "New FDA Migration Cell Used to Study Migration of Styrene from Polystyrene into Various Solvents", Journal of the association of official analytical chemists, The Assocation, Arlington, VA, US, vol. 68, No. 4, Jan. 1, 1985 (Jan. 1, 1985), pp. 770-777, XP009511658, ISSN: 0004-5756.

(Continued)

*Primary Examiner* — Marcus H Taningco
(74) *Attorney, Agent, or Firm* — Hershkovitz & Associates, PLLC; Abraham Hershkovitz; Eugene C. Rzucidlo

(57) ABSTRACT

The present invention relates to a method for determining the migration potential of an at least partially cured energy curing ink and/or varnish printed on a substrate comprising: —providing a substrate, which is printed with the ink and/or varnish, which comprises at least one extractable compound, which absorbs or emits radiation at at least one (Continued)

wavelength between 190 and 3,000 nm, —cutting at least one sample from the printed substrate, placing and incubating the sample in a solvent, in which the extractable compound is soluble, and removing the sample from the solvent to obtain a solvent extract, —quantitatively measuring a spectroscopic characteristic of the solvent extract at at least one wavelength between 190 and 3,000 nm, at which the extractable compound absorbs or emits radiation, so as to obtain a measured numeric value of the spectroscopic characteristic, and —comparing the measured numeric value of the spectroscopic characteristic with a calibration curve.

14 Claims, 5 Drawing Sheets

(51) Int. Cl.
    *G01N 21/31*        (2006.01)
    *G01N 21/84*        (2006.01)
    *G01N 33/32*        (2006.01)

(52) U.S. Cl.
    CPC ......... *G01N 21/8422* (2013.01); *G01N 33/32* (2013.01); *G01N 2001/4061* (2013.01); *G01N 2021/8427* (2013.01)

(58) Field of Classification Search
    CPC ... G01N 2001/4061; G01N 2021/8427; G01N 21/274
    See application file for complete search history.

(56) References Cited

U.S. PATENT DOCUMENTS

| | | |
|---|---|---|
| 7,323,693 B2 | 1/2008 | Naoko et al. |
| 2004/0180226 A1* | 9/2004 | Chatterjee ........... C08F 222/102 428/458 |
| 2009/0301331 A1 | 12/2009 | Laksin et al. |
| 2010/0276578 A1* | 11/2010 | Shelley .............. G01N 21/3563 250/252.1 |
| 2014/0285568 A1* | 9/2014 | Loccufier ............... C09D 11/54 347/20 |
| 2017/0096582 A1* | 4/2017 | Tielemans ........... C08G 18/227 |
| 2017/0204282 A1 | 7/2017 | Illsley et al. |

FOREIGN PATENT DOCUMENTS

| | | |
|---|---|---|
| EP | 2881729 A1 | 6/2015 |
| WO | 2009153045 A1 | 12/2009 |
| WO | 2016007593 A1 | 1/2016 |

OTHER PUBLICATIONS

International Search Report (ISR) in International Application No. PCT/EP2018/059303, dated Jun. 21, 2018.
International Preliminary Report on Patentability (IPRP) in International Application No. PCT/EP2018/059303, dated Jul. 9, 2019.
English language Abstract of EP 2881729 A1 (Jun. 10, 2015).
English language Abstract of CN 102353662 A (Feb. 15, 2012).
Communication pursuant to Article 94(3) EPC in related European Application No. 17 166 008, dated Jul. 11, 2019.

\* cited by examiner

METHOD FOR DETERMINING THE MIGRATION POTENTIAL OF AN AT LEAST PARTIALLY CURED ENERGY CURING INK AND/OR VARNISH PRINTED ON A SUBSTRATE, AND ESPECIALLY OF A PRINTED FOOD PACKING

The present invention relates to a method for determining the migration potential of an at least partially cured energy curing ink and/or of an at least partially cured energy curing varnish printed on a substrate and especially of a printed food packing.

Most of the commercially distributed consumer products are enclosed in a packing, which is often made of paper, cardboard, plastic foil, fabric, metal foil or the like, so as to cover, protect and/or preserve the product. Such packings are predominantly printed with an ink and/or varnish, in order to improve the optical appearance of the packing and in order to present information about the enclosed product. Prominent examples therefore are printed food packings, which present information about the enclosed product, such as about the price, about the size, about the composition, about the nutrients, about the storage life and about the country of origin of the product.

Since it is a function of a food packing to protect the enclosed product, it is a matter of course that a contamination of the product with ingredients of the packing and in particular from the ink and/or varnish, with which the packing is printed, shall be avoided. Such a contamination cannot only harm the quality of the product, such as the taste and smell, but may be even poison the product. This is in particular relevant for primary food packings, which come with their unprinted inner side into direct contact with the enclosed product; in contrast to secondary food packings, which enclose a further packing, in which the product is contained.

On account of these reasons, there are legal guidelines, regulations and norms, which define the maximum allowable migration of such printing inks and varnishes and packings printed therewith, in particular if they are designed to be used for enclosing food.

However, common printing inks and varnishes contain ingredients with a low molecular weight, which thus have a high migration potential and are able to diffuse out of the cured ink or cured varnish, respectively, and through the packing. This applies in particular for energy curing printing inks and varnishes, such as UV curing printing inks and varnishes, i.e. printing inks and varnishes, for which the curing is initiated by UV light. Such printing inks and varnishes include among other compounds photoinitiators, monomers and oligomers, which have a quite low molecular weight and which are thus characterized by a high migration potential. Even cured printing inks and varnishes include—in dependency of their curing degree—more or less non-reacted residues and/or cleavage products of the photoinitiators, monomers and oligomers and have thus a measurable migration potential. Thus, such printing inks and varnishes need to be adequately formulated, so that the completely cured ink and/or varnish contains no or only very small amounts of low molecular weight compounds with a high migration potential. However, even if the printing ink and/or varnish, particularly energy curing printing ink and/or varnish, is formulated so that after complete cure no or only very small amounts of low molecular weight compounds with a high migration potential are included therein, there is still the danger that the printing ink and/or varnish includes too much of such low molecular weight compounds, if it is only partially cured, so that the legally prescribed migration is not met. Such an only partial cure happens, if the drying time and/or drying energy are too low for the given ink and/or varnish wet film thickness.

On account of these reasons, the migration potential of each printed food packing should be determined in order to be on the safe side and to ensure that the migration thereof complies with the legal requirements. The determination of the migration of printing inks applied to the non-food contact side of food packaging materials made from plastics is performed in Europe in accordance with the EU Regulation (EG) No. 1012011 ("Plastics Regulation") and in accordance with the norm EN 1186-13:2002. Paper and board intended to come into contact with food are tested in accordance with EN 14338:2003. Food simulants, which simulate edibles, are used in these tests. The migration potential may be determined by means of the global (or overall) migration or by means of a specific migration. The global migration is an unspecific gravimetrically determined sum parameter, which covers all migratable substances. Thus, the global migration describes the inertness of a packing. In contrast to this, the migration of individual substances is measured with a suitable analysis method, such as gas chromatography combined with mass spectrometry, for determining the specific migration. Specific migration threshold values are defined for each relevant individual substance on the basis of toxicity tests. An example of a measurement method for determining the specific migration is to contact the printed packing on the non-food side to be analysed with the food simulant TENAX® and to store the sample at an elevated temperature for a defined time period. By applying this method, both, invisible set-off and migration through the substrate, are covered. Afterwards, the TENAX® is extracted with solvent, in order to extract the migrated substances, the solvent is removed, the residue is dissolved in a small amount of a suitable solvent and finally qualitatively as well as quantitatively analysed. However, these determinations of the migration are quite laborious, time-consuming and costly.

Alternatively, the curing degree of the printed food packing may be determined, to estimate therefrom the migration potential of the printed food packing. However, such an estimation of the migration potential of the printed food packing from the curing degree is neither precise nor reliable. Methods for determining the curing degree are described for example in U.S. Pat. No. 7,323,693 B2, in U.S. Pat. No. 7,043,326 B2 and in WO 2009/153045 A1. However, these methods only estimate the curing degree of the printed sample, which does not allow any precise and reliable conclusion about the actual migration of the sample. For instance, two differently formulated energy curing inks or varnishes may have the same curing degree, but—due to their different formulation—a completely different migration potential.

In view of all this, the object underlying the present invention is to provide a method for determining the migration potential of an at least partially cured energy curing ink and/or varnish printed on a substrate, such as for determining the migration potential of a printed food packing, which is easy, which is time-efficient and which is cost-efficient, but which nevertheless allows the precise and reliable determination of the migration potential.

In accordance with the present invention, this objective is achieved by providing a method for determining the migration potential of an at least partially cured energy curing ink and/or varnish printed on a substrate and especially of a printed food packing, which comprises the following steps:

a) providing a substrate, which is printed with the at least partially cured energy curing ink and/or at least partially cured energy curing varnish, wherein the at least partially cured energy curing ink and/or at least partially cured energy curing varnish comprises at least one extractable compound, which has a molecular weight of at most 5,000 g/mol and which absorbs or emits radiation at at least one wavelength between 190 and 3,000 nm, b) cutting at least one sample from the printed substrate provided in step a), placing the at least one sample in a solvent, in which at least one of the at least one extractable compound is soluble, incubating the solvent with the at least one sample placed therein for at least 10 seconds and removing the at least one sample from the solvent to obtain a solvent extract, c) optionally, recording a spectrum for at least a part of the wavelength range between 190 and 3,000 nm of the solvent extract, d) quantitatively measuring a spectroscopic characteristic of the solvent extract at at least one wavelength between 190 and 3,000 nm, at which at least one of the at least one extractable compound absorbs or emits radiation, so as to obtain a measured numeric value of the spectroscopic characteristic and e) comparing the measured numeric value of the spectroscopic characteristic with a calibration curve, in which for at least one printed substrate, in which the same energy curing ink and/or energy curing varnish is printed on the same substrate as in step a), the correlation between
  i) the results of a migration test regarding the overall migration limit and/or of the migration of specific compound(s) of the at least one printed substrate and
  ii) a numeric value of the spectroscopic characteristic measured at the same wavelength as in step d) of a solvent extract obtained from a sample of the at least one printed substrate by performing step b),
is shown in dependency of the curing degree of the energy curing ink and/or energy curing varnish so as to obtain the migration potential.

This solution is based on the surprising finding that by simply extracting the migratable low molecular weight compounds from a substrate, which is printed with an at least partially cured energy curing ink and/or varnish, into a solvent so as to obtain a solvent extract and by quantitatively measuring a spectroscopic characteristic, such as the extinction, absorbance or transmittance, of the solvent extract, the migration potential of the printed substrate can be precisely and reliably determined in an easy, time-efficient and cost-efficient manner, if the measured numeric value of the spectroscopic characteristic is compared with the aforementioned calibration curve, in which for the same ink/varnish-substrate-system or primer/ink/varnish-substrate system the results of a migration test are correlated to the numeric value of the spectroscopic characteristic in dependency of the curing degree. Because the numeric value of the spectroscopic characteristic quantitatively measured in step d) is obtained from the solvent extract, which has been provided in step b) and which includes—apart from the solvent—only the extractable compounds to be quantitatively determined, a falsification of the result due to other components disturbing the measurement is reliably avoided. In contrast to this, a quantitative measurement of the spectroscopic characteristic of the at least partially cured energy curing ink would bear the risk of a falsification of the result, for instance since other components of the ink in addition to the extractable compounds absorb at the measurement wavelength and thus pretend a higher value as that caused by the relevant extractable compounds. So, in the method in accordance with the present invention for each of these systems only one such calibration curve has to be determined, in order to allow to measure precisely and reliably the migration potential for the respective system, independently, from where and under which conditions it has been prepared. For instance, the manufacturer of the energy curing ink may produce for each of a plurality of substrates, which are printed with the ink, such a calibration curve and distribute the calibration curves together with the energy curing ink to his customers. Any of the customers can then, after having printed and dried the substrate, such as food packing, with the ink, easily, precisely and reliably determine the actual migration potential of the printed substrate by simply incubating a piece of the printed substrate in for instance ethanol e.g. for five minutes, then measuring e.g. the transmittance of the solvent extract and finally comparing the measured numeric value of the transmittance with the calibration curve, which has been delivered from the manufacturer of the ink.

The formulation "determining the migration potential of an at least partially cured energy curing ink and/or varnish" means in accordance with the present invention to "quantitatively determine the amount of extractable compounds having a molecular weight of at most 5000 g/mol in at least partially cured energy curing ink and/or varnish". In turn, molecular weight is defined in the present invention as weight average molecular weight measured with gel permeation chromatography using a polystyrene standard.

It is noted that the migratable components are also denoted in the present invention as extractable compounds, wherein an extractable compound is defined in accordance with the present invention—as set out above—as compound having a molecular weight of at most 5,000 g/mol.

Principally, the printed substrate provided in step a) may be produced by any method known to a person skilled in the art. Usually, it will be prepared by printing the at least partially cured energy curing ink and/or at least partially cured energy curing varnish at a determined printed weight and/or at a determined print speed onto the substrate followed by energy curing.

The energy curing ink or varnish is preferably a crosslinkable ink or varnish, respectively. However, the present invention is not limited to an ink or varnish, respectively, which cures by crosslinking.

A particular advantage of the method in accordance with the present invention is that it is universally applicable and in particular essentially not limited with regard to the kind and material of the substrate and with regard to the kind and composition of the ink and/or varnish, and with regard to the drying or curing method, respectively. Good examples are in particular obtained, when the substrate is selected from the group consisting of papers, cardboards, plastic foils, glass, nonwovens, fabrics, tissues, metal foils, metal sheets and arbitrary combinations of two or more of the aforementioned substrates.

Suitable examples for the kind of the energy curing ink and/or energy curing varnish are those, which are selected from the group consisting of offset printing inks, offset printing varnishes, flexographic printing inks, flexographic printing varnishes, digital printing inks and varnishes, inkjet inks and varnishes, screen inks and varnishes, primers, hot melt coatings, extrusion coatings, coatings applied by coil coating, curtain coatings, sprayings and arbitrary combinations of two or more of the aforementioned inks and/or varnishes. Preferably, the energy curing ink and/or energy curing varnish is a radiation curing ink and/or radiation curing varnish and more preferably the energy curing ink and/or energy curing varnish is an UV curing ink and/or UV curing varnish.

Any energy curing ink and/or varnish, such as UV curing ink and/or varnish, includes as migratable substance a curing initiator, namely in the case of an UV curing ink and/or varnish, a photoinitiator. The residual amount of non-reacted photoinitiator and/or cleavage products thereof in the cured or partially cured ink and/or varnish, respectively, will be—in dependency of the concentration of the photoinitiator included in the uncured ink and/or varnish, respectively, as well as in dependency of the curing degree of the ink and/or varnish, respectively, —more or less. The residual non-consumed photoinitiator and/or cleavage products thereof is one of the migratable components of the cured or partially cured ink and/or varnish, respectively. As set out above, the migratable component is also denoted in the present invention as extractable compound, which is defined in accordance with the present invention as compound having a molecular weight of at most 5,000 g/mol. The method in accordance with the present invention is applicable for any curing initiator and particularly photoinitiator, which can be spectroscopically quantified for example by means of an absorption measurement, an extinction measurement, a transmittance measurement or a fluorescence measurement at a suitable wavelength. Accordingly, the at least partially cured energy curing ink and/or at least partially cured energy curing varnish may comprise as photoinitiator a compound selected from the group consisting of benzophenones, α-hydroxy ketones, α-alkoxyketones, α-aminoketones, aminoalkylphenones, acyl phosphine oxides, bisacylphosphinoxides, dialkylamines, thioxanthones, multifunctional amino benzoates, benzildimethylketals, phosphine oxides, 2-benzyl-2-dimethyl-amino-1-(4-morpholinophenyl)-butanone-1, 2-benzyl-2-dimethylamino-1-(4-morpholinophenyl)-butanone-1, acetophenones, methyl-o-benzoyl-benzoate, methylbenzoylformate, 2-methyl-1-(4-methylthiophenyl)-2-morpholinpropan-1-one, 2-ethylhexyl-4-dimethylaminobenzoate, ethyl-4-dimethylaminobenzoate, N-methyldiethanolamine, polymeric aminobenzoate derivatives, polymeric benzophenone derivatives, polymeric thioxanthone derivatives, camphorquinone and arbitrary combinations of two or more of the aforementioned compounds.

For cationic curing systems, blocked Lewis or Broensted acids, like bis-(($C_{10}$-$C_{14}$)alkylphenyl)-iodoniumhexafluoroantimonate, bis-(4,4-dodecylphenyl)-iodoniumhexafluorophosphate or bis-(4-methyl-phenyl)-iodoniumhexafluorophosphate, are suitable.

Another important source of migratable compounds remaining in the cured or partially cured ink and/or varnish, respectively, is non-reacted monomer and/or oligomer. The method in accordance with the present invention is applicable for any monomer and/or oligomer, which can be quantified by chromatographic analysis methods in a migration test. In view thereof, the at least partially cured energy curing ink and/or at least partially cured energy curing varnish may comprise at least one radically polymerizable monomer and/or at least one radically polymerizable oligomer, which is selected from the group consisting of acrylates, such as propoxylate (4) glycerol triacrylate, trimethylolpropantriacrylate, ethoxylated trimethylolpropane triacrylate, propoxylated trimethylolpropane triacrylate, pentaerythritol triacrylate, pentaerythritol(4)-propoxylated-triacrylate, tri-functional monomers, such as Laromer types from BASF or Ebecryl 2047 or Ebecryl 12 from Allnex, ditrimethylolpropane tetraacrylate, pentyerythritol-tetraacrylate, ethoxylated pentaerythrioltetraacrylate, dipentaerythritol-pentaacrylate, dipentaerythritol hexaacrylate, oxiranes and arbitrary combinations of two or more of the aforementioned substances.

Since the method in accordance with the present invention uses for the quantitative determination of the migration potential of the printed substrate the comparison of a spectroscopic measurement value and a calibration curve, in which the migration potential of this system is correlated with the numeric value of the spectroscopic characteristic for the same system in dependency of the curing degree of the ink and/or varnish, respectively, the method in accordance with the present invention is suitable to determine the migration potential independently from the molecular weight of the migratable compound. The method in accordance with the present invention is in particular suitable to determine the migration potential of a printed substrate of an ink and/or varnish, respectively, which includes at least one extractable compound having a molecular weight of at most 2,000 g/mol and even of at most 1,000 g/mol. The molecular weight of a compound is the weight average molecular weight measured according to the present invention by gel permeation chromatography using a polystyrene standard.

Preferably, the extractable compounds are no atoms and no heavy metal ions of Au, Ag, Pt, Ga, Th, Hf, Ru, In, Cd, Hg and Pb. More preferably, the extractable compounds are molecules, even more preferably organic molecules and most preferably organic molecules comprising at least 5 carbon atoms per molecule.

The method in accordance with the present invention is particularly suitable for UV curing inks and/or varnishes. Therefore, at least one of the at least one extractable compound absorbs or emits radiation at at least one wavelength between 190 and 3,000 nm, preferably between 190 and 1,500 nm, more preferably 190 and 800 nm, even more preferably between 250 and 600 nm, even more preferably between 250 and 450 nm, still more preferably between 250 and 400 nm and most preferably between 250 and 350 nm.

In a further development of the idea of the present invention, it is proposed that in step b) one sample is cut from the printed substrate, wherein the sample has a surface of 0.01 to 100 $cm^2$, preferably of 0.1 to 10 $cm^2$, more preferably of 0.25 to 5 $cm^2$ and most preferably of 0.5 to 4 $cm^2$, This embodiment is particularly suitable for substrates, which are homogeneously printed with the ink and/or varnish, respectively, i.e. in which the thickness of the ink and/or varnish, respectively, is homogeneous over the whole surface of the substrate.

However, for substrates, which are inhomogeneously printed with the ink and/or varnish, respectively, i.e. in which the thickness of the ink and/or varnish, respectively, varies, it is preferred that in step b) two or more samples are cut from the printed substrate, wherein the samples have a total surface of 0.01 to 100 $cm^2$, preferably of 0.1 to 10 $cm^2$, more preferably of 0.25 to 5 $cm^2$ and most preferably of 0.5 to 4 $cm^2$. In this case, an average value is obtained from the different samples.

Any solvent may be used in step b) of the method in accordance with the present invention, in which the extractable compound has a sufficiently high solubility. Good results are particularly obtained, when at least one of the at least one extractable compound has at ambient temperature a solubility in the solvent of at least 0.1 mg/l, preferably of at least 0.3 mg/l, even more preferably of at least 0.5 mg/l and most preferably of at least 1 mg/l. Preferably, all of the at least one extractable compound have at ambient temperature a solubility in the solvent of at least 0.1 mg/l, preferably of at least 0.3 mg/l, even more preferably of at least 0.5 mg/l and most preferably of at least 1 mg/l.

Examples for suitable solvents are those, which are selected from the group consisting of alcohols, water-alcohol mixtures, ketones, esters, ethers, alkanes, cycloalkanes, aromatic solvents, tetrahydrofurane, dioxane and arbitrary combinations of two or more of the aforementioned substances.

Particularly suitable solvents are alcohols or water-alcohol mixtures, wherein the alcohol is preferably a $C_{1-10}$-alcohol, more preferably a $C_{1-6}$-alcohol, even more preferably a $C_{1-4}$-alcohol and most preferably ethanol.

Preferably, the sample is placed in step b) in a volume of solvent, which is at least 1 ml solvent per $cm^2$ sample, preferably 2 to 100 ml solvent per $cm^2$ sample, more preferably 2 to 50 ml solvent per $cm^2$ sample, even more preferably 2.5 to 20 ml solvent per $cm^2$ sample and most preferably 2.5 to 12.5 nil solvent per $cm^2$ sample. This assures that enough solvent is present to extract necessary quantities of the extractable compounds within reasonable time.

The present invention is not particularly limited concerning the time period, for which the sample is incubated in step b) in the solvent. Good results are e.g. obtained, when the sample is incubated in step b) for 30 seconds to 5 hours, preferably for 1 to 60 minutes, more preferably for 2 to 10 minutes and most preferably for 4 to 6 minutes.

In order to allow the extractable compound(s) in step (b) to diffuse into the solvent without mechanically releasing the cured ink and/or varnish, respectively, from the substrate, it is preferred that the incubation in step b) is performed without agitation of the solvent, in which the sample is placed, and at ambient temperature. Alternatively, the incubation in step b) may be performed with gently agitating the solvent. However, in the latter case care should be taken that the cured ink and/or varnish, respectively, is not mechanically released from the substrate in this method step.

The method step c) of recording a spectrum for at least a part of the wavelength range between 190 and 3,000 nm of the solvent extract, is merely optional and not mandatory for carrying out the method in accordance with the present invention. It is only required if the operator of the method in accordance with the present invention does not know the kind of migratable or extractable compounds, which are contained in the ink and/or varnish, respectively, and thus has to determine by means of the spectrum to be recorded in step c) at which wavelength he may perform the quantitative measurement of the spectroscopic characteristic in step d). Thus, if the operator of the method in accordance with the present invention knows the kind of migratable or extractable compounds, which are contained in the ink and/or varnish, respectively, or if he got information from the supplier of the ink and/or varnish, respectively, at which wavelength the quantitative measurement of the spectroscopic characteristic in step d) shall be performed, step c) must not be conducted.

As set out above, the method in accordance with the present invention is particularly suitable for UV curing inks and varnishes. Therefore, when the optional method step c) is performed, the spectrum in step c) is recorded for at least a part of the wavelength range between 190 and 3,000 nm, preferably between 190 and 1,500 nm, more preferably between 190 and 800 nm, even more preferably between 250 and 600 nm, yet more preferably between 250 and 450 nm, still more preferably between 250 and 400 nm and most preferably between 250 and 350 nm.

In a further development of the idea of the present invention, it is proposed that the spectroscopic characteristic of the solvent extract is measured in step d) at a wavelength, at which the numeric value of the spectroscopic characteristic is at least 50% of the peak maximum of the spectroscopic characteristic in the spectrum of the solvent extract, from which preferably the respective spectrum of the solvent has been subtracted. The subtraction of the respective spectrum of the solvent from the spectrum measured from the solvent extract in step d) assures that the measurement is not falsified by the spectroscopic characteristics of the solvent and that indeed any peak in the spectrum of the solvent extract is that of an extractable compound from the ink and/or varnish, respectively, and not from the solvent.

In accordance with a particular preferred embodiment of the present invention, the spectroscopic characteristic, which is quantitatively measured in step d), is selected from the group consisting of extinction, transmittance, absorbance, fluorescence and arbitrary combinations of two or more thereof.

More preferably, the spectroscopic characteristic, which is quantitatively measured in step d), is the extinction or transmittance of the solvent extract. Such extinction and transmittance measurements may be made in standard apparatuses available in most of the laboratories.

In the latter embodiment, it is preferred that the extinction or transmittance of the solvent extract is measured in step d) at a wavelength, at which the numeric value of the extinction or of transmittance is at least 50% of the peak maximum of the extinction or transmittance spectrum, from which the respective spectrum of the solvent has been subtracted. Again, the subtraction of the respective spectrum of the solvent from the spectrum measured in step d) assures that the measurement is not falsified by the spectroscopic characteristics of the solvent and that indeed any peak in the spectrum of the solvent extract is that of an extractable compound from the ink and/or varnish, respectively, and not from the solvent.

Even more preferably, the extinction or transmittance of the solvent extract is measured in step d) at the wavelength of the peak maximum of the extinction or transmittance spectrum, from which the respective spectrum of the solvent has been subtracted.

If two or more migratable compounds are included in the ink and/or varnish, respectively, —such as in the case of an ink and/or varnish, respectively, which comprises two or more different photoinitiators—only one of these, some of these or all of these may be detected with the method in accordance with the present invention. If only one of the contained migratable compounds shall be detected, step d) is performed by using a wavelength, at which this compounds absorbs or emits radiation. If some or all of the migratable compounds shall be detected, step d) may be performed by using one wavelength, at which all these compounds absorb or emit radiation. Alternatively, step d) may be performed by using two or more different wavelengths selected so that all these compounds absorb or emit radiation at at least one of these wavelengths.

In accordance with a particular preferred embodiment of the present invention, the calibration curve used in step e) has been prepared i) by determining the overall migration and/or the specific migration of one or more migrating compound(s) for different printed substrates (subsequently also referred in this context as "print proof"), in which for each of the different printed substrates the same energy curing ink and/or energy curing varnish has been printed on the same substrate as in step a), wherein each of the different printed substrates has been cured to a different curing degree, ii) by obtaining for each of the different printed substrates a solvent extract by performing step b) and by determining for each of these solvent extracts the extinction or transmittance at the same wavelength as in step d) and iii) by correlating the respective data obtained in steps i) and ii) into a graph.

As set out above, different printed substrates mean in this context that one and the same substrate is printed with one and the same ink, wherein, any of these printed substrates had a different curing degree.

Of course, the more print proofs are used for preparing the calibration curve, the more precise is the calibration curve. On the other hand, the more print proofs are used for preparing the calibration curve, the more time consuming and laborious is the preparation of the calibration curve, A good compromise between both tendencies is to use 2 to 100, preferably 2 to 20, more preferably 3 to 10 and most preferably 3 to 7 different print proofs for preparing the calibration curve.

If the migrants in the ink and/or varnish, respectively, are known to the operator of the method, a suitable wavelength to be used in step d) can be derived from known spectra of the respective migratable compounds. However, if the migrants in the ink and/or varnish, respectively, are not known to the operator of the method, the migrants have to be first identified, before determining a suitable wavelength to be used in step d).

The curing of each of the different print proofs to a different curing degree may be achieved by printing the energy curing ink and/or energy curing varnish for each of the different print proofs with a different printed weight and/or with a different printing speed and/or with a different wet film thickness and/or with a different curing energy dose onto the substrate and then by drying the different print proofs under the same conditions, i.e. for the same drying time at the same drying temperature, i.e. with the application of the same drying energy dose. In tendency, based on a given curing energy dose, i.e. a given curing speed and a given UV lamp power and a given drying temperature, the curing degree of a printed substrate is the lower, the higher the printed weight of ink and/or varnish, respectively, is on the substrate. Likewise, based on a given drying energy dose, the curing degree of a printed substrate is the lower, the higher the wet film thickness of ink and/or varnish, respectively, is on the substrate. However, based on a given energy dose, the curing degree of a printed substrate is the higher, the lower the printing speed of ink and/or varnish, respectively, is.

Alternatively, the curing of each of the different print proofs to a different curing degree may be achieved by printing the energy curing ink and/or energy curing varnish for each of the different print proofs with the same printed weight, with the same printing speed and with the same wet film thickness onto the substrate and then by drying the different printed substrates under different conditions, i.e. for different drying times, with different UV lamp powers and/or at different drying temperatures, i.e. with a different energy dose. Of course, the curing degree of a printed substrate is the higher, the higher the energy dose applied during the curing is, i.e. the longer the drying time and/or the higher the drying temperature is.

Of course, the both aforementioned embodiments may be combined, i.e. the curing of each of the different printed substrates to a different curing degree may be achieved by printing the energy curing ink and/or energy curing varnish for each of the different printed substrates with a different printed weight and/or with a different printing speed and/or with a different wet film thickness onto the substrate and then by drying the different printed substrates under different conditions, i.e. for different drying times and/or at different drying temperatures, i.e. with different energy doses.

In accordance with a particular preferred embodiment of the present invention the calibration curve used in step e) has been prepared i) by determining the overall migration and/or the specific migration of one or more migrating compound(s) for different printed substrates, in which for each of the different printed substrates the same energy curing ink and/or energy curing varnish has been printed on the same substrate as in step a) for each of the different printed substrates with a different printed weight and/or with a different printing speed and/or with a different wet film thickness and/or with a different curing energy dose onto the substrate, wherein each of the different printed substrates has been cured with the same drying energy dose for the same drying time and the same drying temperature, ii) by obtaining for each of the different printed substrates a solvent extract by performing step b) and by determining for each of these solvent extracts the extinction or transmittance at the same wavelength as in step d) and iii) by correlating the respective data obtained in steps i) and ii) into a graph.

As set out above, different printed substrates mean in this context that one and the same substrate is printed with one and the same ink, wherein, any of these printed substrates had a different curing degree.

In accordance with an alternative preferred embodiment of the present invention the calibration curve used in step e) has been prepared i) by determining the overall migration and/or the specific migration of one or more migrating compound(s) for different printed substrates, in which for each of the different printed substrates the same energy curing ink and/or energy curing varnish has been printed on the same substrate as in step a) for each of the different printed substrates with the same printed weight, with the same printing speed and with the same wet film thickness onto the substrate, wherein each of the different printed substrates has been dried with a different energy dose, such as for example a different drying time and/or a different curing speed and/or a different UV lamp power and/or a different drying temperature, ii) by obtaining for each of the different printed substrates a solvent extract by performing step b) and by determining for each of these solvent extracts the extinction or transmittance at the same wavelength as in step d) and iii) by correlating the respective data obtained in steps i) and ii) into a graph.

In a further development of the idea of the present invention, it is proposed that the overall and specific migration is measured in accordance with the EU Regulation (EG) No. October 2011 ("Plastics Regulation") and to the norms EN 1186-13:2002 and EN 14338:2003, Suitable food simulants to be used in these measurements are particularly modified polyphenylene oxide available under the brand name Tenax®, plant oils, aqueous solutions of 10% by weight ethanol, of 20% by weight ethanol, of 50% by weight ethanol or of 3% by weight acetic acid.

Subsequently, the present invention is described by means of an illustrating, but not limiting example.

EXAMPLE

UV offset printing inks with following components were prepared:

| | | |
|---|---|---|
| Pigment Black 7 | Pigment Black 7 | 19.0% |
| Pigment Blue 15:3 | Pigment Blue 15:3 | 2.0% |
| Ebecryl LEO 10801 | reactive Epoxyacrylate | 16.0% |
| Ebecryl LEO 10601 | reactive Polyester Acrylate polymer | 30.0% |
| Ebecryl Leo 10501 | diluting reactive acrylate | 10.0% |
| Pentaerythritol triacrylate | functional reactive polyol acrylate oligomer | 6.0% |
| Photoinitiator mixture* | Photoinitiator mixture* | 8.0% |
| EHA** | aminobenzoate co-initiator | 3.0% |
| Ceridust 3620 | wax | 1.3% |
| BHT*** | stabilizer | 0.2% |
| Genorad 19 | stabilizer | 0.1% |
| ASP 600 | filler | 4.4% |

*Photoinitiator-Mixture: Irgacure 369 (3%), Speedcure 7005 (2.5%), Omnipol TX (2.0%), Irgacure 819 (0.5%)
**2-Ethylhexyl-4-dimethylaminobenzoate
***Butylhydroxytoluene (2,6-Di-tert-butyl-4-methylphenol)

Preparation of Laboratory Print Proofs:

Inks were printed on coated paper (220 g/m², format 4.6×23 cm) using a Prüfbau test printer with a printing speed of 0.5 m/s and cured with an integrated UV lamp (curing speed: 0.1 m/s). The ink quantity on the substrate (printing weight in g/m²) was determined by weighing the inked print form before and after printing. Samples with printing weight 1 g/m²; 1.5 g/m² and 2 g/m² were prepared.

Extraction of Print Proofs and UV/VIS-Measurements.

Directly after printing a sample of 1 cm×1 cm was cut out of the print proof and set into a solution of 10 mL EtOH at a temperature of 21° C. To obtain the solvent extract, the cut out sample was removed after 5 minutes.

A solvent extract from unprinted substrate was used as a reference sample applying identical conditions for the extraction as for the printed samples.

To find the optimal wavelength for the UV/VIS measurements an UV/VIS-spectra of the solvent extract of the printed sample and the reference sample were determined with a dual beam UV/VIS-spectrometer (Perkin Elmer Lambda 2) in a range of 250 to 500 nm at room temperature. The resulting spectrum is shown in FIG. 1.

The difference of the sample $E(\lambda)_{sample}$ and reference spectrum $E(\lambda)_{reference}$, results in the corrected spectrum of the printed sample $E(\lambda)_{corrected}$.

$$E(\lambda)_{corrected} = E(\lambda)_{sample} - E(\lambda)_{reference} \quad (1)$$

At a wavelength of 310 nm the maximal absorption was observed in the corrected spectrum. This wavelength was defined as the measurement wavelength for the determination of the absorption of the solvent extracts. Results are given as the corrected absorption at 310 nm: E(310 nm).

The absorption at 310 nm E(310 nm) was measured for different printing weights. With an increasing printing weight the degree of curing is decreased which leads to higher absorption values E (310 nm), as shown in the subsequent table 1.

TABLE 1

Absorption at 310 nm E(310 nm) of the solvent extracts from samples with different printing weights. E(310 nm)

| Printing weight [g/m2] | E(310 nm) |
|---|---|
| 1 | 0.014 |
| 1.5 | 0.033 |
| 2 | 0.055 |

These values are also shown in FIG. 2.

Migration Testing

The level of migrating substances was determined by a set-off migration using modified polyphenylene oxide (brand name Tenax®) as a food simulant test according to DIN EN 14338:2003. Therefore, for each ink 5 sheets of laboratory print proofs were stacked and stored under pressure (2 kg/dm²) for 6 days at room temperature. The three inner sheets of the stack were used for the migration test. The samples were cut (1 dm²) and put into a petri dish (Ø14 cm) with the printed surface downwards. A glass ring was put onto the sample (outer diameter of the glass ring Ø13 cm, wall thickness 0.5 cm, height 1 cm). 3 g of Tenax® powder (60/80 Mesh) were distributed evenly on the sample (non-printed side) inside the glass ring. The petri dish was closed with a lid, wrapped in aluminum foil and stored in an oven for 10 days at 60° C.

The Tenax® was extracted with acetone for 40 min in a Soxhlet extractor. The acetone is distilled off, the dried residue is solved in 1 mL ethanol containing C13/C24-alkane standard (50 µg/mL) and analysed by GC-MS and LC-MS. For known and migration-relevant components (acrylates, photoinitiators, photoinitiator cleavage products) the analysis is carried out with reference standard solutions of these components. The results are presented as the amount of migratable substances present in 1 kg of food [mg/kg food] according to the EU cube model (assumption: 1 kg food is packed into 6 dm²).

The migration results for the aminobenzoate co-initiator and a polyol acrylate are shown in Table 2 and in FIGS. 3 and 4. An increasing printing weight leads to a lower degree of curing, resulting in larger amounts of migrants.

TABLE 2

Migration of aminobenzoate co-initiator at migration test conditions: 60° C., 10 days, Tenax in mg/kg food (assumption: 1 kg food is packed into 6 dm²)

| Printing weight [g/m2] | Aminobenzoate co-inititiator [mg/kg food] | Polyol Acrylate [mg/kg food] |
|---|---|---|
| 1 | 0.46 | 0.11 |
| 1.5 | 1.01 | 0.47 |
| 2 | 2.20 | 1.05 |

Calibration Curve—Correlation of Migration and Absorption Results

For the determination of the calibration curve the results of the migration test were plotted against the absorption E(310 nm) from the solvent extracts for aminobenzoate co-iniator and for the polyol acrylate. The result is shown in FIG. 5.

As can be seen from FIG. 5, for both substances there is a linear correlation of migration and absorption E(310 nm) with a coefficient of determination ($R^2$) of 97% (Amino benzoate co-initiator) and 99% (Polyol Acrylate).

Calculation of Migration

The estimated migration can be calculated from the absorption E(310 nm) using the determined linear regression equation for aminobenzoate co-initiator (equation 2) and for polyol Acrylate (equation 3):

$$\text{Migration[mg/kg food]} = 42{,}55 * E(310\text{ nm}) - 0.2134 \qquad \text{equation (2)}$$

$$\text{Migration[mg/kg food]} = 22{,}908 * E(310\text{ nm}) - 0.2302 \qquad \text{equation (3)}$$

Figure 1:
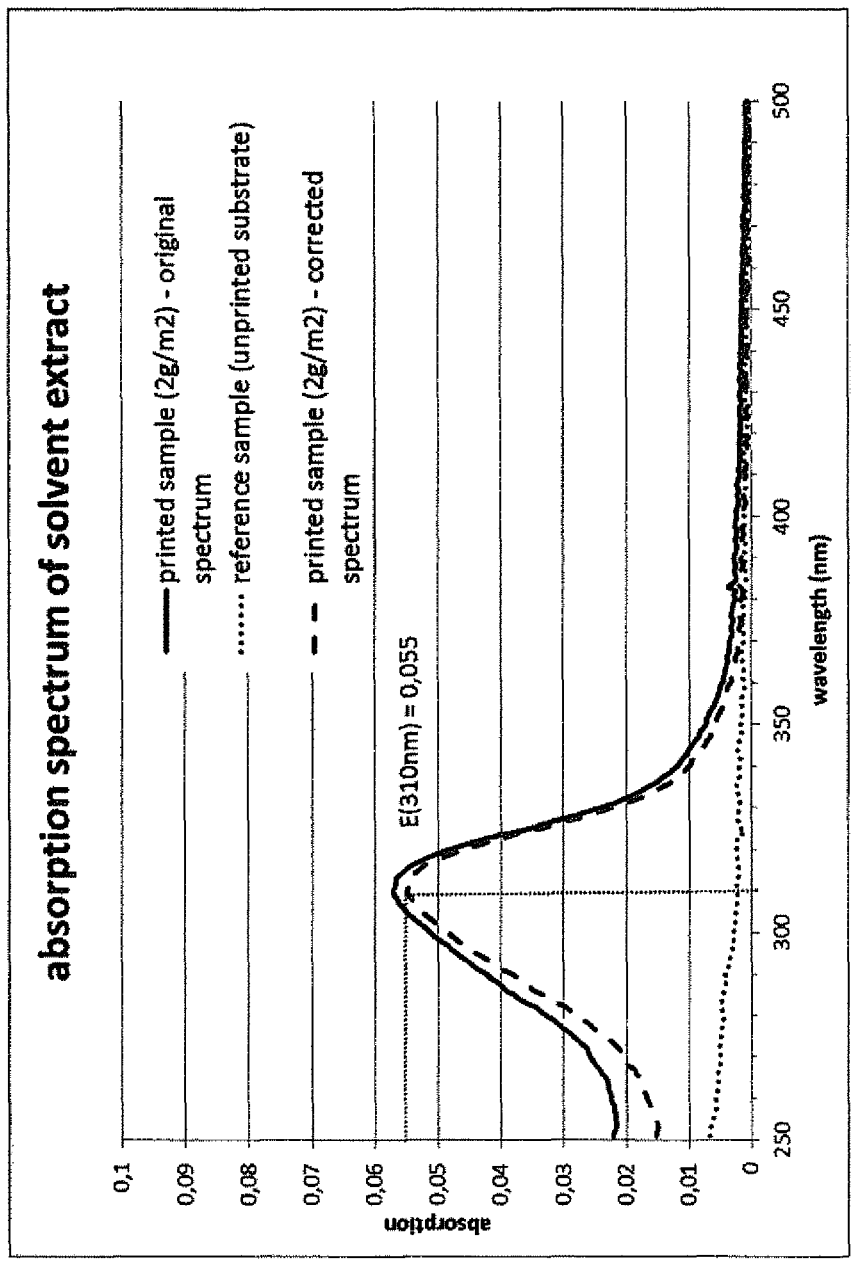
FIG. 1 shows the UV/VIS-spectra of the solvent extracts of (i) the printed sample, (ii) the reference sample (unprinted substrate) and (iii) the difference spectrum of (i) and (ii) of the example.
Figure 2:
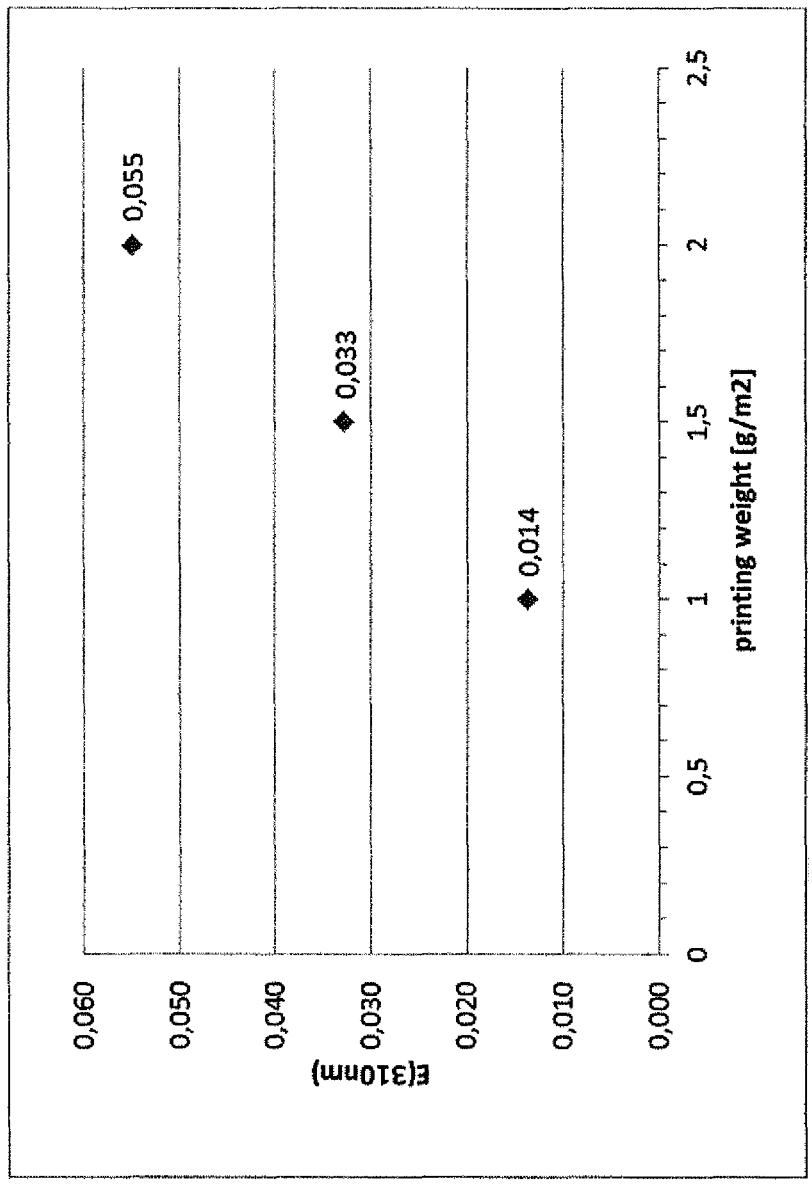
FIG. 2 shows the corrected absorption at 310 nm from solvent extracts of printed samples at different printing weights of the example.
Figure 3:
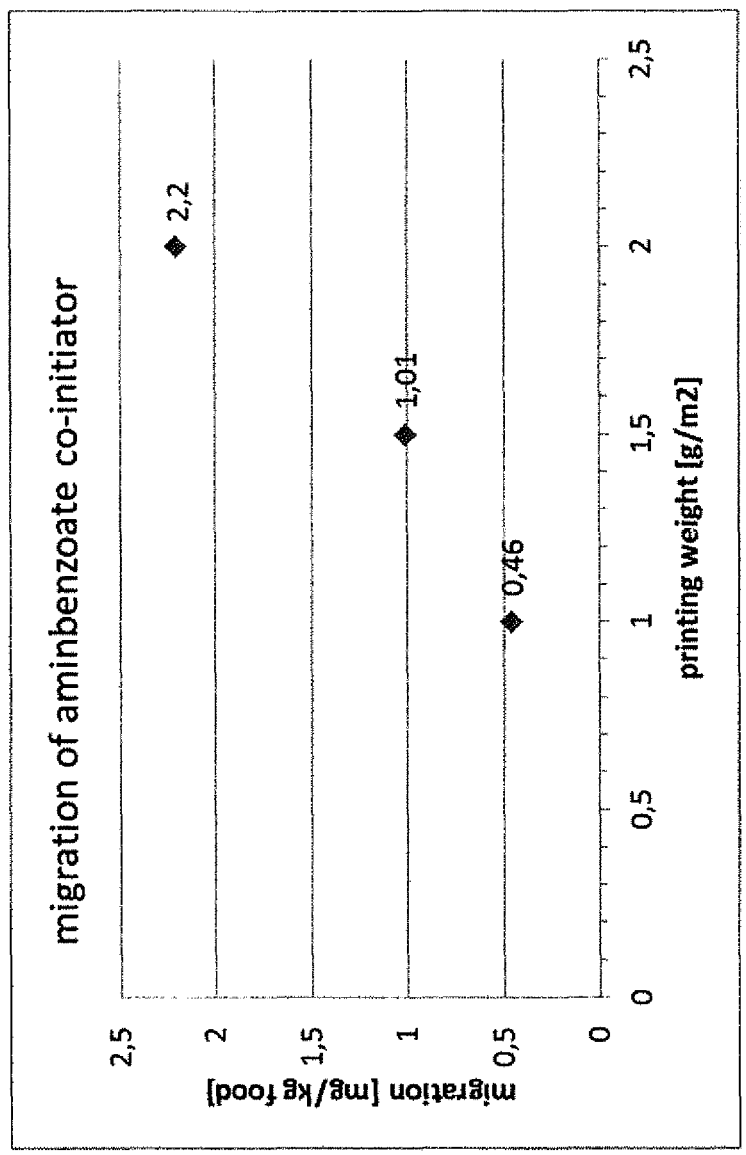
FIG. 3 shows the migration of aminobenzoate co-initiator at migration test conditions: 60° C., 10 days, Tenax in mg/kg food (assumption: 1 kg food is packed into 6 dm$^2$), for different printing weight.
Figure 4:
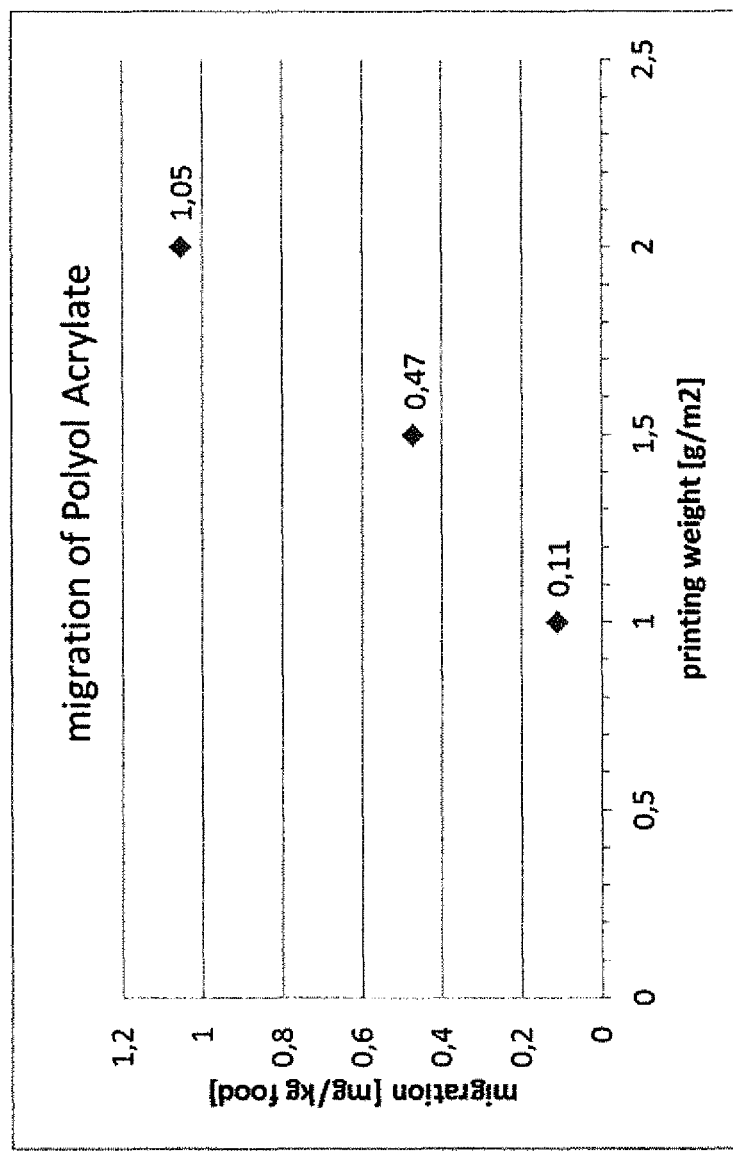
FIG. 4 shows the migration of poylol acrylate at migration test conditions: 60° C., 10 days, Tenax in mg/kg food (assumption: 1 kg food is packed into 6 dm$^2$), for different printing weight.
Figure 5:
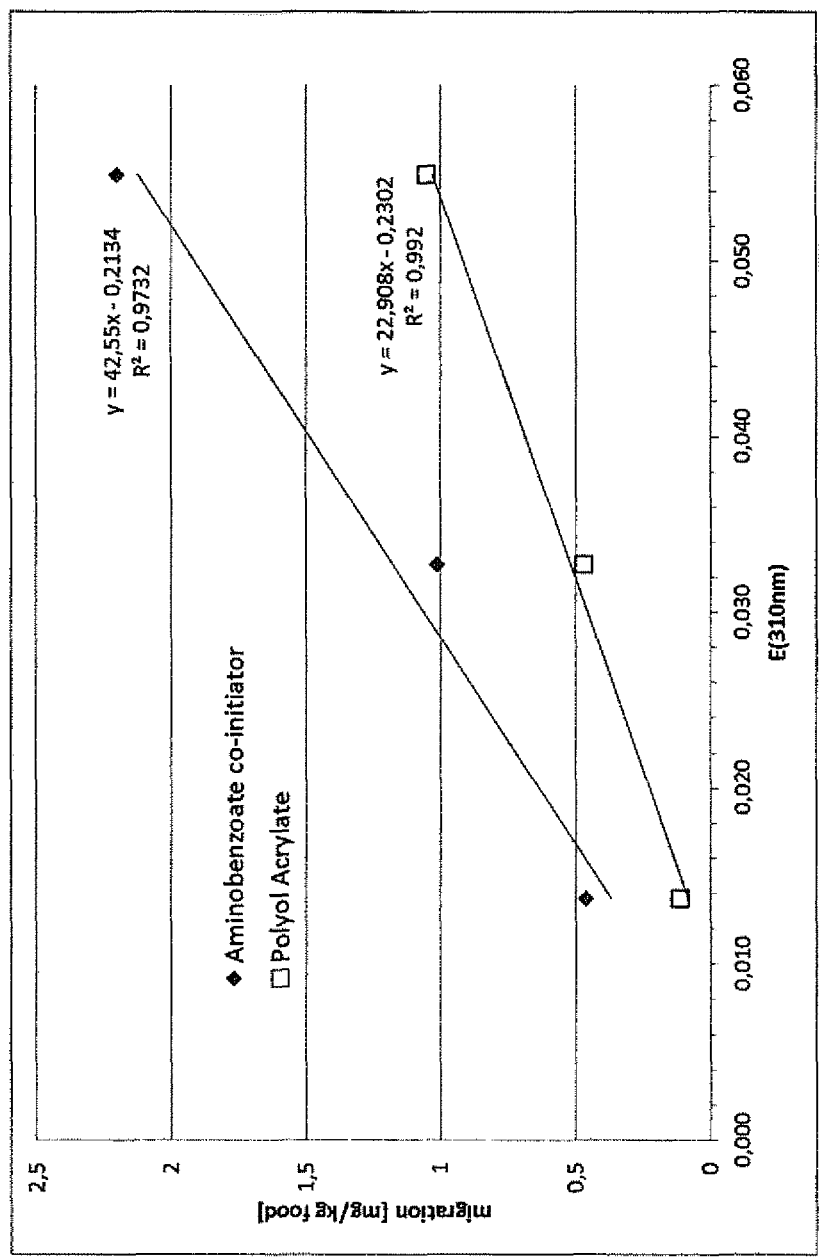
FIG. 5 shows the calibration curve of the migration of aminobenzoate co-initiator and polyol acrylate against the corrected absorption at 310 nm of the solvent extracts obtained in the example

The invention claimed is:

1. A method for determining the migration potential of an at least partially cured energy curing ink and/or varnish printed on a substrate and especially of a printed food packing, which comprises the following steps:
   a) providing a substrate, which is printed with the at least partially cured energy curing ink and/or at least partially cured energy curing varnish, wherein the at least partially cured energy curing ink and/or at least partially cured energy curing varnish comprises at least one extractable compound, which has a molecular weight of at most 5,000 g/mol and which absorbs or emits radiation at at least one wavelength between 190 and 3,000 nm,
   b) cutting at least one sample from the printed substrate provided in step a), placing the at least one sample in a solvent, in which at least one of the at least one extractable compound is soluble, incubating the solvent with the at least one sample placed therein for at least 10 seconds and removing the at least one sample from the solvent to obtain a solvent extract,
   c) optionally, recording a spectrum for at least a part of the wavelength range between 190 and 3,000 nm of the solvent extract,
   d) quantitatively measuring a spectroscopic characteristic of the solvent extract at at least one wavelength between 190 and 3,000 nm, at which at least one of the at least one extractable compound absorbs or emits radiation, so as to obtain a measured numeric value of the spectroscopic characteristic and
   e) comparing the measured numeric value of the spectroscopic characteristic with a calibration curve, in which for at least one printed substrate, in which the same energy curing ink and/or energy curing varnish is printed on the same substrate as in step a), the correlation between
      i) the results of a migration test regarding the overall migration and/or of the migration of specific compound(s) of the at least one printed substrate and
      ii) a numeric value of the spectroscopic characteristic measured at the same wavelength as in step d) of a solvent extract obtained from a sample of the at least one printed substrate by performing step b),
   is shown in dependency of the curing degree of the energy curing ink and/or energy curing varnish so as to obtain the migration potential, wherein the calibration curve used in step e) has been prepared
      iii) by determining the overall migration and/or the specific migration of one or more migrating compound(s) for different printed substrates, in which for each of the different printed substrates the same energy curing ink and/or energy curing varnish has been printed on the same substrate as in step a), wherein each of the different printed substrates has been cured to a different curing degree,
      iv) by obtaining for each of the different printed substrates a solvent extract by performing step b) and by determining for each of these solvent extracts the extinction or transmittance at the same wavelength as in step d) and
      v) by correlating the respective data obtained in steps iii) and iv) into a graph.

2. The method in accordance with claim 1, wherein the substrate is selected from the group consisting of papers, cardboards, plastic foils, glass, nonwovens, fabrics, tissues, metal foils, metal sheets and arbitrary combinations of two or more of the aforementioned substrates.

3. The method in accordance with claim 1, wherein the solvent is an alcohol or a water-alcohol mixture, wherein the alcohol is a $C_{1-10}$-alcohol.

4. The method in accordance with claim 1, wherein the sample is incubated in step b) for 30 seconds to 5 hours.

5. The method in accordance with claim 1, wherein step c) is performed and the spectrum in step c) is recorded for at least a part of the wavelength range between 190 and 1,500 nm.

6. The method in accordance with claim 1, wherein the spectroscopic characteristic of the solvent extract is measured in step d) at a wavelength, at which the numeric value of the spectroscopic characteristic is at least 50% of the peak maximum of the spectroscopic characteristic in the spectrum of the solvent extract, from which the respective spectrum of the solvent has been subtracted.

7. The method in accordance with claim 1, wherein the spectroscopic characteristic, which is quantitatively measured in step d), is selected from the group consisting of extinction, transmittance, absorbance, fluorescence and arbitrary combinations of two or more thereof.

8. The method in accordance with claim 7, wherein the spectroscopic characteristic, which is quantitatively measured in step d), is the extinction or transmittance of the solvent extract.

9. The method in accordance with claim 8, wherein the extinction or transmittance of the solvent extract is measured in step d) at a wavelength, at which the numeric value of the extinction or of the transmittance is at least 50% of the peak maximum of the extinction or transmittance spectrum, from which the respective spectrum of the solvent has been subtracted.

10. The method in accordance with claim 9, wherein the extinction or transmittance of the solvent extract is measured in step d) at the wavelength of the peak maximum of the extinction or transmittance spectrum, from which the respective spectrum of the solvent has been subtracted.

11. The method in accordance with claim 1, wherein the curing of each of the different printed substrates to a different curing degree is achieved by printing the energy curing ink and/or energy curing varnish for each of the different printed substrates with a different printed weight and/or with a different printing speed, with a different wet film thickness and/or with a different curing energy dose onto the substrate and then by drying the different printed substrates under the same conditions.

12. The method in accordance with claim 1, wherein the curing of each of the different printed substrates to a different curing degree is achieved by printing the energy curing ink and/or energy curing varnish for each of the different printed substrates with the same printed weight, with the same printing speed and with the same wet film thickness onto the substrate and then by drying the different printed substrates under different conditions, namely for different drying times, with different curing speeds, with different UV lamp powers and/or at different drying temperatures.

13. The method in accordance with claim 1, wherein the calibration curve used in step e) has been prepared
   i) by determining the overall migration and/or the specific migration of one or more migrating compound(s) for different printed substrates, in which for each of the different printed substrates the same energy curing ink and/or energy curing varnish has been printed on the same substrate as in step a) for each of the different printed substrates with a different printed weight and/or with a different printing speed and/or with a different wet film thickness onto the substrate, wherein each of the different printed substrates has been cured under the same conditions,
   ii) by obtaining for each of the different printed substrates a solvent extract by performing step b) and by determining for each of these solvent extracts the extinction or transmittance at the same wavelength as in step d) and
   iii) by correlating the respective data obtained in steps i) and ii) into a graph.

14. The method in accordance with claim 1, wherein the overall and specific migration is measured in accordance with norms EN 1186:13:2002 and EN14338:2003.

* * * * *